United States Patent

Rae et al.

[11] Patent Number: 5,128,340
[45] Date of Patent: Jul. 7, 1992

[54] THIAZOLE DERIVATIVES

[75] Inventors: Duncan R. Rae, Lanark; Samuel G. Gibson, Motherwell, both of Scotland

[73] Assignee: Akzo N.V., Arnhem, Netherlands

[21] Appl. No.: 700,331

[22] Filed: May 6, 1991

Related U.S. Application Data

[63] Continuation of Ser. No. 432,711, Nov. 7, 1989, abandoned.

[30] Foreign Application Priority Data

Nov. 8, 1988 [EP] European Pat. Off. .......... 88.310471

[51] Int. Cl.$^5$ ............... C07D 417/04; A61K 31/445
[52] U.S. Cl. ................. 514/235.5; 514/255; 514/256; 514/318; 514/341; 514/342; 544/124; 544/333; 544/364; 546/193; 546/278; 546/280
[58] Field of Search .......... 546/280, 278, 193; 544/333, 124, 364; 514/341, 342, 235.5, 255, 256, 318

[56] References Cited

U.S. PATENT DOCUMENTS 4,650,805  3/1987  Jaen et al. ........................ 546/280
4,739,067  4/1988  Jaen et al. ........................ 546/280

FOREIGN PATENT DOCUMENTS 0244018  11/1987  European Pat. Off. .
0280873  1/1988   European Pat. Off. .
3703435  8/1988   Fed. Rep. of Germany .

*Primary Examiner*—Robert Gerstl
*Attorney, Agent, or Firm*—Donna Bobrowicz; William M. Blackstone

[57] ABSTRACT

The invention relates to thiazole derivatives with the general formula I

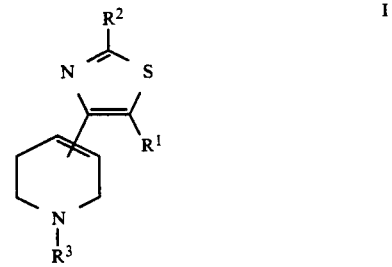

wherein
  $R^1$ is halogen, $CF_3$, CN, $NO_2$, OH or $C_1$–$C_6$ alkoxy;
  $R^2$ is hydrogen, $C_1$–$C_6$ alkyl, $C_1$–$C_6$ alkoxy, aryl, $C_6$–$C_{13}$ aralkyl, an unsubstituted amino group, a substituted amino group, or an amino group which is part of a 5- or 6-membered ring;
  $R^3$ is $C_1$–$C_6$ hydrocarbon, $C_6$–$C_{13}$ aralkyl, $C_2$–$C_7$ alkoxyalkyl or $C_1$–$C_{13}$ acyl; and their pharmaceutically acceptable acid addition salts.

These new compounds have $\alpha_2$-antagonist activity without dopamine agonist activity and as such are specifically useful for the treatment of depression and other related illnesses, e.g. for treating patients with anxiety disorders and cognitive disturbances.

14 Claims, No Drawings

THIAZOLE DERIVATIVES

This is a continuation of application Ser. No. 07/432,711 filed Nov. 7, 1989, now abandoned.

The invention relates to thiazole derivatives with the general formula I

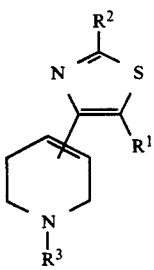

wherein $R^1$ is halogen, $CF_3$, CN, $NO_2$, OH or $C_1$-$C_6$ alkoxy;

$R^2$ is hydrogen, $C_1$-$C_6$ alkyl, $C_1$-$C_6$ alkoxy, aryl, $C_6$-$C_{13}$ aralkyl, an unsubstituted amino group, a substituted amino group, or an amino group which is part of a 5- or 6-membered ring;

$R^3$ is $C_1$-$C_6$ hydrocarbon, $C_6$-$C_{13}$ aralkyl, $C_2$-$C_7$ alkoxyalkyl or $C_1$-$C_{13}$ acyl;

and their pharmaceutically acceptable acid addition salts.

These new compounds have $\alpha_2$-adrenergic receptor antagonist activity without dopamine agonist activity and may have 5-$HT_{1A}$ receptor activity and as such are specifically useful for the treatment of depression and other related illnesses, e.g. for treating patients with anxiety disorders and cognitive disturbances.

Preferred compounds are compounds of formula I wherein $R^1$ is halogen (F, Cl, Br or I) or CN, $R^2$ is an unsubstituted or substituted amino group and $R^3$ is e.g. methyl, ethyl, propyl, n-butyl ($C_1$-$C_4$ alkyl) or arylethyl. Among the preferred compounds the compounds with the most suitable profile of activity, are those with $R^1$ is Cl or CN and wherein the thiazole is connected with a tetrahydropyridine through position 3 of said latter moiety.

The term $C_1$-$C_6$ alkyl, used in the definition of formula I, means an alkyl group with 1 to 6 carbon atoms, such as methyl, ethyl, propyl, isopropyl, n-butyl, isobutyl, tert-butyl, pentyl and hexyl. Alkyl groups with 1 to 4 carbon atoms are preferred.

The term $C_1$-$C_6$ alkoxy means an alkoxy group with 1 to 6 carbon atoms, in which the meaning of the alkyl constituent is the same as above. Preferred alkoxy groups have 1 to 4 carbon atoms.

The term aryl means an aromatic group such as phenyl, naphthyl, pyridyl, thienyl, and the like which may be unsubstituted or substituted with OH, halogen, $CF_3$, CN, $NO_2$, $C_1$-$C_6$ alkyl or $C_1$-$C_6$ alkoxy.

The term $C_6$-$C_{13}$ aralkyl, used in the definition of formula I, means an aralkyl group with 6 to 13 carbon atoms, in which the meanings of the alkyl and aryl constituents are the same as those of the above-mentioned $C_1$-$C_6$ alkyl and aryl groups.

The term substituted amino means an amino group substituted by $C_1$-$C_6$ alkyl, $C_1$-$C_{13}$ acyl, aryl, $C_6$-$C_{13}$ aralkyl, alkyloxycarbonyl, alkenyloxycarbonyl or aralkyloxycarbonyl. The amino group may be part of a 5- or 6-membered ring such as pyrrolidine, imidazolidine, pyrimidine, morpholine, piperidine, unsubstituted or N-($C_1$-$C_6$ alkyl) substituted piperazine, and the like.

The term $C_2$-$C_7$ alkoxyalkyl means an alkoxyalkyl group with 2 to 7 carbon atoms, in which the meanings of the alkyl and alkoxy constituents are the same as above. Alkoxyalkyl groups with 2 to 5 carbons, such as methoxyethyl, ethoxyethyl, isopropoxymethyl, are preferred.

The alkyl and aralkyl moieties in the alkyloxycarbonyl and aralkyloxycarbonyl groups are $C_1$-$C_6$ alkyl and $C_6$-$C_{13}$ aralkyl groups respectively, as defined above. The alkenyl moiety in the alkenyloxycarbonyl group is an alkenyl group with 2 to 6, and preferably 2 to 4 carbon atoms, like vinyl, allyl and 2-propenyl.

The term $C_1$-$C_6$ hydrocarbon, used in the definition of $R^3$, means a saturated or unsaturated, branched or straight-chained hydrocarbon with 1 to 6 carbon atoms, and preferably 1 to 4 carbon atoms. Examples are methyl, ethyl, isopentyl, allyl, ethynyl and the like.

The term $C_1$-$C_{13}$ acyl means an acyl group derived from an aliphatic or araliphatic carboxylic acid with 1-13 carbon atoms, such as formic acid, acetic acid, propionic acid, phenylacetic acid, cinnamic acid and the like.

The compounds according to this invention are usually obtained as acid addition salts, which are derived from pharmaceutically acceptable acids, such as hydrochloric acid, sulphuric acid, phosphoric acid, acetic acid, propionic acid, glycolic acid, maleic acid, fumaric acid, malonic acid, succinic acid, tartaric acid, lactic acid, citric acid, ascorbic acid, salicylic acid, benzoic acid, methanesulphonic acid, and the like. Acid addition salts may be obtained by reaction of the free base according to formula I with an appropriate acid in a suitable solvent.

The compounds of this invention may be prepared by any method known for the preparation of analogous compounds.

Convenient starting products for the synthesis of compounds according to formula I, are thiazole derivatives with general formula II:

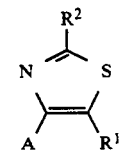

wherein $R^1$ and $R^2$ have the aforesaid meanings, and A represents a 3- or 4-pyridyl moiety.

Compounds of formula II may, among other methods, be prepared by condensing a 3- or 4-pyridine derivative of formula III

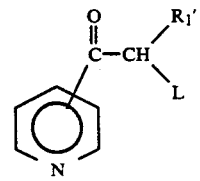

wherein $R_1'$ may be hydrogen or one of the groups selected from $R^1$, as defined before, and L is a suitable leaving group like halogen or a sulphonyl derivative, and preferably bromine, with a compound of formula IV

wherein $R^2$ has the aforesaid meaning. When $R_1'$ is hydrogen, the required group $R^1$ may be introduced after the condensation of III and IV.

A suitable synthesis for the preparation of compounds with formula II wherein $R^1$ is CN is the condensation of compounds of general formula V

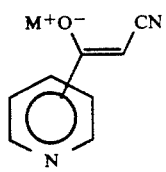

wherein M is an alkali or an alkaline earth metal, e.g. sodium, potassium, calcium, magnesium and the like, with a compound of formula IV, preferably in the presence of iodine.

For the preparation of compounds of formula I the pyridine moiety of the compounds of formula II is to be reduced by using methods commonly applied for the reduction of pyridines, for instance by preparing a quaternary pyridinium salt using a suitable alkyl- or aralkyl-halide to give the preferred group $R^3$, followed by reaction with an appropriate reducing agent, such as sodium borohydride.

Compounds of formula I in which $R^3$ is acyl, can be obtained by cleaving the alkyl- or aralkyl group which is attached to the nitrogen of the tetrahydropyridine moiety, followed by acylation in a manner commonly used for the acylation of an amino group. The preferred quaternary group is the benzyl group, which can easily be cleaved by e.g. ethyl chloroformate or catalytic reduction.

Where $R^2$ in formula I represents an amino group it is very convenient to start with a compound of formula II, wherein $R^2$ represents a protected amino group, for instance the formylamino group, and $R^1$ and A have the aforesaid meanings. After applying the above-mentioned reduction procedure the amino group can be freed by using any method known for the cleavage of the protective group. A formyl group, for example, may be cleaved by refluxing the formylamino compound in a mixture of methanol and hydrazine hydrate.

Compounds of formula I wherein $R^2$ is amino can be converted into substituted amino derivatives according to the general formula I by using known methods, e.g. reaction with alkyl-, aryl- or aralkylhalides or by reductive alkylation.

Compounds with formula I wherein $R^2$ represents an alkyloxycarbonyl, alkenyloxycarbonyl or aralkyloxycarbonyl substituted amino group can conveniently be prepared from a compound with formula I wherein $R^2$ represents a formylamino group or an amino group, by reaction of said compound with formula I with an alkyl-, alkenyl- or aralkyl-chloroformate.

Compounds of formula I wherein $R^2$ is H may be prepared from the amino derivatives ($R^2$ is $NH_2$) by deamination with nitrous acid.

Compounds of formula I, as obtained by any of the methods known for analogous compounds, usually are converted into a pharmaceutically acceptable salt, by applying well-known methods comprising the free base of compounds of formula I and an appropriate organic or inorganic acid in a suitable solvent.

Compounds according to this invention can be administered either enterally, locally or parenterally, in a daily dose between 0.01 and 50 mg/kg body weight, and preferably between 0.1 and 10 mg/kg body weight. For human use a daily dose between 5 and 500 mg is preferred. For this purpose the compounds are processed in a form suitable for enteral, local or parenteral administration, for example a tablet, pill, capsule, suppository, solution, emulsion, paste or spray. The oral form is the most preferred form of administration.

The following examples further illustrate the preparation of the compounds used in this invention.

EXAMPLE 1 a) A solution of thiourea (70,4 g) in water (265 ml) was added dropwise to a stirred solution of 3-bromoacetylpyridine hydrobromide (251,6 g) in water (1 l) over 15 minutes. The solution, which turned yellow and became quite hot, was allowed to stand for one hour, and was then basified by addition of aqueous ammonia. The resulting solid was filtered off, washed with water, and dried in vacuo at 65° C. to give 4-(pyridin-3-yl)-thiazol-2-amine, (155 g) Mp 200° C.

b) N-Chlorosuccinimide (14,7 g) was added all at once to a solution of 4-(pyridin-3-yl)-thiazol-2-amine (17,7 g) in N,N-dimethylformamide (130 ml) at 0°-5° C. After five minutes, the product precipitated, and after ten minutes, precipitation was completed by addition of water and ammonium hydroxide solution. The product was filtered and dried in vacuo at 60° C. to give 5-chloro-4-(pyridin-3-yl)-thiazol-2-amine, (18,2 g) Mp 202° C.

c) 5-Chloro-4-(pyridin-3-yl)-thiazol-2-amine (20 g) was dissolved in formic acid (40 ml) and formamide (20 ml) and the mixture was heated at 90° C. for six hours. After cooling, the mixture was diluted with water (240 ml) and basified with aqueous ammonia solution. The resulting solid was isolated by filtration, and dried in vacuo at 60° C. to give N-[5-chloro-4-(pyridin-3-yl)-thiazol-2-yl]-formamide, (22,8 g) Mp 229° C.

d) A suspension of the formamide (10 g—as prepared in c) in acetonitrile was heated at reflux for five hours with iodomethane (10 ml). The cooled mixture was diluted with ether and the resulting solid was filtered off and dried in vacuo at 60° C. to give 3-(5-chloro-2-formylaminothiazol-4-yl)-1-methylpyridium iodide (13,9 g) Mp 255° C.

e) Sodium borohydride (12,5 g) was added portionwise over forty five minutes to a stirred suspension of the quaternary salt (25 g—as prepared in d) in methanol (500 ml) which had been precooled below 10° C. After a further fifteen minutes, the resulting solution was neutralized with acetic acid, then most of the solvent was evaporated under reduced pressure. The residue was dissolved in water and the solution was basified with ammonia to give a solid which was isolated by filtration (12,5 g). The crude product was dissolved in ethanol (125 ml) and the solution was heated under reflux for four hours. Most of the solvent was removed by evaporation under reduced pressure, then the product was precipitated by addition of water. After isolation, the crude product was recrystallized from methanol to give N-[5-chloro-4-(1,2,5,6-tetrahydro-1-methylpyridin-3-yl)-thiazol-2-yl]-formamide (6,5 g) Mp 193° C.

EXAMPLE 2

The product of Example 1e was converted with fumaric acid into
N-[5-chloro-4-(1,2,5,6-tetrahydro-1-methylpyridin-3-yl)-thiazol-2-yl]-formamide (E)-2-butenedioate (1:1) Mp 168° C.

EXAMPLE 3

In a similar manner as described in Examples 1 and 2 the following compound is prepared:
N-[5-chloro-4-(1,2,5,6-tetrahydro-1-propylpyridin-3-yl)-thiazol-2-yl]-formamide hydrochloride Mp 240° C. (dec.).

EXAMPLE 4

A suspension of the formamide (6,5 g—as prepared in Example 1e) in methanol (65 ml) and hydrazine hydrate (3,25 ml) was heated under reflux for three hours. The resulting solution was evaporated to small volume under reduced pressure, then the residue was diluted with water to give a solid which was isolated by filtration and dried in vacuo at 25° C. At this stage the crude product was purified (if necessary) by chromatography on silica using dichloromethane containing an increasing proportion of methanol.

The resulting free base was then converted to the fumaric acid salt and purified by crystallization from a suitable solvent mixture to give 5-chloro-4-(1,2,5,6-tetrahydro-1-methylpyridin-3-yl)-thiazol-2-amine (E)-2butenedioate (2:1) (5,1 g) Mp 170° C.

EXAMPLE 5

In a similar manner as described in Example 4 the following compounds are prepared:
5-chloro-4-(1-ethyl-1,2,5,6-tetrahydropyridin-3-yl)-thiazol-2-amine (E)-2-butenedioate (1:1) Mp 131° C. (dec);
5-chloro-4-(1,2,5,6-tetrahydro-1-propylpyridin-3-yl)-thiazol-2-amine (E)-2-butenedioate (1:1) Mp 143° C.;
5-chloro-4-[1,2,5,6-tetrahydro-1-(1-methylethyl)-pyridin-3-yl]-thiazol-2-amine (E)-2-butenedioate (1:1) Mp 139° C.;
5-chloro-4-(1-butyl-1,2,5,6-tetrahydropyridin-3-yl]-thiazol-2-amine (E)-2-butenedioate (1:1) Mp 141° C.;
5-chloro-4-[1,2,5,6-tetrahydro-1-(2-propenyl)-pyridin-3yl]-thiazol-2-amine (E)-2-butenedioate (1:1) Mp 138° C.;
5-chloro-4-[1,2,5,6-tetrahydro-1-(phenylmethyl)-pyridin-3-yl]-thiazol-2-amine (E)-2-butenedioate (1:1) Mp 163° C.;
5-chloro-4-[1-(4-chlorophenylmethyl)-1,2,5,6-tetrahydropyridin-3-yl]-thiazol-2-amine (E)-2-butenedioate (1:1) Mp 128° C.;
5-chloro-4-[1,2,5,6-tetrahydro-1-(2-phenylethyl)-pyridin-3-yl]-thiazol-2-amine (E)-2-butenedioate (1:1) Mp 141° C.;
5-chloro-4-(1,2,5,6-tetrahydro-1-propylpyridin-3-yl)-N-methylthiazol-2-amine (Z)-2-butenedioate (1:1) Mp 171° C.;
5-chloro-4-(1,2,5,6-tetrahydro-1-propylpyridin-3-yl)-N-(1-methylethyl)-thiazol-2-amine (E)-2-butenedioate (1:1) Mp 133° C.;
5-chloro-4-(1,2,5,6-tetrahydro-1-propylpyridin-3-yl)-N,N-dimethylthiazol-2-amine hydrochloride Mp 150° C.;
5-chloro-4-(1,2,5,6-tetrahydro-1-methylpyridin-3-yl)-2-(4-methylpiperazin-1-yl)-thiazole hydrochloride (1:2);
5-chloro-4-[1,2,5,6-tetrahydro-1-(2-methoxyethyl)pyridin-3-yl]-thiazol-2-amine (E)-2-butenedioate (1:1) Mp 120° C.;
5-chloro-4-[1,2,5,6-tetrahydro-1-(2-pyridin-2-ylethyl)-pyridin-3-yl]-thiazol-2-amine (E)-2-butenedioate (1:1) Mp 152° C.

EXAMPLE 6

A solution of 5-chloro-4-(1,2,5,6-tetrahydro-1-methylpyridin-3-yl)-thiazol-2-amine (5 g—as prepared in Example 1) in 5N sulphuric acid (30 ml) was added (dropwise) simultaneously with a solution of sodium nitrite in water, to a mixture of sulphuric acid (30 ml) and hypophosphorous acid (6,5 ml), and kept below 5° C.

When the addition had been completed the reaction mixture was neutralized by portionwise addition of sodium carbonate. The resulting mixture was filtered through "dicalite" and the filtrate was extracted with ethylacetate. Evaporation of the extract gave the product as a dark oil which was purified by chromatography on silica with dichloromethane containing an increasing proportion of ether and then methanol. The purified material was converted to the fumarate salt and recrystallized from methanol/ether to give 0,65 g of 5-chloro-4-(1,2,5,6-tetrahydro-1-methylpyridin-3-yl)-thiazole (E)-2-butenedioate (1:1). Mp 136° C.

EXAMPLE 7

A solution of 5-chloro-4-[1,2,5,6-tetrahydro-1-(phenylmethyl)pyridin-3-yl]-thiazol-2-amine (10 g—as prepared in Example 5) in dichloromethane (400 ml) was stirred below 5° C. with sodium carbonate (3.1 g) while vinyl chloroformate (3,7 ml) was added dropwise over twenty minutes. After a further twenty minutes water was added and the layers were separated. The organic phase was evaporated to a gum which was purified by chromatography on silica, eluting with dichloromethane/methanol.

The first two products off the column (the bis- and monovinyl carbamates respectively) were combined (6 g) and dissolved in dry dioxan (240 ml) and a little hydrogen chloride was passed into the solution which was then allowed to stand at room temperature for two hours. Ethanol (240 ml) was then added and the solution was left to stand overnight. The resulting solid was filtered off and dried in vacuo at 60° C. to give 5-chloro-4-(1,2,5,6-tetrahydropyridin-3-yl)-thiazol-2-amine dihydrochloride (1,7 g). Mp 201° C. (decomp.).

EXAMPLE 8 a) A solution of thioacetamide (5 g) in methanol (25 ml) was added dropwise to a stirred suspension of 3-bromoacetylpyridine hydrobromide (17,75 g) in methanol (89 ml) at room temperature over ten minutes. After about one hour, the hydrobromide of the product crystallized out. The mixture was diluted with ether (100 ml) and the product was isolated by filtration. The solid was dissolved in water and the solution was basified with ammonium hydroxide. The product was extracted into ether and the extract was washed with saturated salt solution, then evaporated to give 2-methyl-4-(pyridin-3-yl)-thiazole as a crystalline solid (8,6 g) Mp 81° C.

b) N-Chlorosuccinimide (3,8 g) was added to a solution of 2-methyl-4-(pyridin-3-yl)-thiazole (5 g) in N,N- dimethylformamide (25 ml) at room temperature. A further addition (1,9 g) of the reagent was made after four hours, then the reaction solution was allowed to stand at room temperature for forty eight hours.

The mixture was diluted with water (150 ml) and sodium sulphite solution was added till the mixture was negative to starch/iodide. The product was then extracted into ether and the extract was washed with water and evaporated to give 5-chloro-2-methyl-4-(pyridin-3-yl)-thiazole (5,1 g) as a brown oil.

c) Using the methods outlined in Examples 1, 2 and 4, 5-chloro-2-methyl-4-(pyridin-3-yl)-thiazole was converted to 5-chloro-4-(1,2,5,6-tetrahydro-1-propylpyridin-3-yl)-2-methyl thiazole (E)-2-butenedioate (1:1). Mp 132° C.

EXAMPLE 9

In a similar manner as described in Example 8 was prepared:
5-chloro-4-(1,2,5,6-tetrahydro-1-propylpyridin-3-yl)-2-phenylthiazole (Z)-2-butenedioate (1:1) Mp 172° C.

EXAMPLE 10

The sodium salt of 3-(2-cyanoacetyl)-pyridine (35 g, 0,2 mol), was suspended in dioxan (508 ml), and neutralised by the addition of glacial acetic acid (11,9 ml, 0,2 mol). Thiourea (31,6 g, 0,52 mol) and iodine were added to the suspension (52,7 g, 0,21 mol), and the mixture was stirred at 55° C. under an atmosphere of nitrogen for 3¼ hours. The solvent was removed under reduced pressure, water (500 ml) was added, giving a suspension which was basified with 33% NH$_3$ solution. The product was filtered and washed with water, giving an off-white solid, (27,4 g, 65% yield). Mp 230° C. (dec.).

In a similar manner as outlined in Examples 1d, 1e and 2 this product was converted into 2-amino-4-(1,2,5,6-tetrahydro-1-methyl-pyridin-3-yl)-thiazole-5-carbonitrile hydrochloride, Mp 242° C. (dec.).

EXAMPLE 11

In a similar manner as described in Example 10 was prepared:
2-amino-4-(1-ethyl-1,2,5,6-tetrahydropyridin-3-yl)-thiazole-5-carbonitrile (Z)-2-butenedioate (1:1) Mp 195° C.
2-amino-4-(1-butyl-1,2,5,6-tetrahydropyridin-3-yl)-thiazole-5-carbonitrile (Z)-2-butenedioate (1:1) Mp 185° C.
2-amino-4-[1,2,5,6-tetrahydro-1-(2-phenylethyl)pyridin-3-yl]-thiazole-5-carbonitrile (E)-2-butenedioate (2:1) Mp 188° C.
2amino-4-[1,2,5,6-tetrahydro-1-[2-(3-methoxyphenyl)-ethyl]pyridin-3-yl]-thiazole-5-carbonitrile dihydrochloride. Mp 128° C.
2amino-4-[1-[2-(4-fluorophenyl)ethyl]-1,2,5,6-tetrahydropyridin-3-yl]thiazole-5-carbonitrile (E)-2-butenedioate (2:1) Mp 171° C.

EXAMPLE 12

In a similar manner as described in Example 10 the sodium salt of 4-(2-cyanoacetyl)-pyridine was converted into 2-amino-4-(1-butyl-1,2,3,6-tetrahydropyridin-4-yl)-thiazole-5-carbonitrile (Z)-2-butenedioate (1:1). Mp 198° C.

EXAMPLE 13

To a stirred solution of 3-(bromoacetyl)-pyridine hydrobromide (5,6 g, 0,02 mol) in water (30 ml) was added 0-methyl thiocarbamate (1,82 g, 0,02 mol) and stirring was continued in a water bath at approximately 40° C. until a solution was obtained, which was cooled, and allowed to stand overnight at room temperature. The solution was extracted with ethyl acetate, and the organic layer was discarded. The aqueous layer was carefully adjusted to pH 7,5 using 5% Na$_2$CO$_3$ solution and the product separated as an oil.

The oil was extracted into ethyl acetate, the organic layer was dried (Na$_2$SO$_4$), evaporated under reduced pressure, and the semisolid residue was chromatographed over silica yielding 2,9 g (76%) of an oil.

In a manner similar as outlined in Example 1b the oil was chlorinated and the product was then reacted with iodomethane and reduced with sodium borohydride, using similar methods as outlined in Example 1d and e affording, after conversion to the salt, 3-[4-(5-chloro-2-methoxythiazolyl]-1-methyl-1,2,5,6-tetrahydropyridine (Z)-2-butenedioate (1:1). Mp 111° C.

EXAMPLE 14

Vinyl chloroformate (1,9 ml) followed by triethylamine (8,3 ml) were added to a suspension of N-[ 5-chloro-4-(1-methyl-1,2,5,6-tetrahydropyridin-3-yl)-2-thiazolyl]formamide (4,4 g; Example 1e) in methylene chloride (170 ml) and the resulting solution was stirred at room temperature for 15 mins. Water (87 ml) was added to the mixture and the methylene chloride layer was separated, washed with water, dried over Na$_2$SO$_4$ and evaporated to give a gum (5,1 g) which was chromatographed on silica to give pure material (1,61 g). This was converted to the maleate salt in the usual manner to give crystalline ethenyl 5-chloro-4-[1,2,5,6-tetrahydro-1-methyl-pyridin-3-yl]thiazol-2-carbamate (Z)-2-butenedioate (1:1). Mp 164° C.

EXAMPLE 15

In a similar manner as described in Examples 1 and 2 4-bromoacetylpyridine hydrobromide was converted into
5-chloro-4-(1,2,3,6-tetrahydro-1-methylpyridin-4-yl)-thiazol-2-amine (Z)-2-butenedioate (1:1) Mp 190° C. (dec.).
5-chloro-4-(1-butyl-1,2,3,6-tetrahydropyridin-4-yl)-thiazol-2-amine (Z)-2-butenedioate (1:1) Mp 196° C.

EXAMPLE 16 a) A suspension of 10 g of 5-chloro-4-(pyridin-3-yl)-thiazol-2-amine (obtained in Example 1b) in 50 ml of butyronitrile was heated at reflux for 2 h with 10 ml of iodomethane. After cooling down of the mixture, the resulting solid was filtered off and recrystallized from methanol to give 13,3 g of 3-(2-amino-5-chlorothiazol-4-yl)-1-methylpyridinium iodide.

b) 200 mg of sodium borohydride were added portionwise over 1 h to a stirred suspension of 400 mg of 3-(2-amino-5-chlorothiazol-4-yl)-1-methylpyridinium iodide in 25 ml of water which had been precooled at 5° C. After 3 h the resulting solid was filtered off, washed with diethyl ether and sucked dry. After treatment with fumaric acid 5-chloro-4-(1,2,5,6-tetrahydro-1-methyl-pyridin-3-yl)-thiazol-2-amine (E)-2-butenedioate (2:1), mp 170° C., was obtained.

We claim:
1. Thiazole derivatives comprising the general formula:

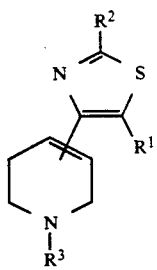

[I]

wherein
$R^1$ is a halogen, $CF_3$, CN, $NO_3$, OH or $C_1$–$C_6$ alkoxy;
$R^2$ is hydrogen, $C_1$–$C_6$ alkyl, $C_1$–$C_6$ alkoxy, phenyl, naphthyl, pyridyl, thienyl or amino, wherein the phenyl, naphthyl, pyridyl and thienyl may be substituted by OH, halogen, $CF_3$, CN, $NO_2$, $C_1$–$C_6$ alkyl or $C_1$–$C_6$ alkoxy, and wherein the amino may be substituted by $C_1$–$C_6$ alkyl, $C_1$–$C_{13}$ acyl, phenyl, naphthyl, pyridyl, thienyl, $C_6$–$C_{13}$ aralkyl, $C_2$–$C_7$ alkyloxy-carbonyl, $C_3$–$C_7$, alkenyloxycarbonyl, $C_7$–$C_{14}$ alkyloxy-carbonyl, or wherein $R^2$ is a substituted amino group, the nitrogen atom of which is part of a 5 or 6 membered ring selected from the group consisting of pyrrolidine, imidazolidine, pyrimidine, morpholine, piperidine, piperazine and N—($C_1$–$C_6$ alkyl) substituted piperazine; and
$R^3$ is $C_1$–$C_6$ hydrocarbon, $C_6$–$C_{13}$ aralkyl, $C_2$–$C_7$ alkoxy-alkyl or $C_1$–$C_{13}$ acyl;
and their pharmaceutically acceptable acid addition salts.

2. Thiazole derivatives according to claim 1, wherein $R^1$ is a halogen or CN, $R^2$ is an unsubstituted or substituted amino group, and $R^3$ is $C_1$–$C_4$ alkyl or arylethyl.

3. Thiazole derivatives according to claim 2, wherein $R^1$ is Cl and the thiazole is connected to position 3 of the tetrahydropyridine.

4. Thiazole derivatives according to claim 2, wherein $R^1$ is CN and the thiazole is connected to position 3 of the tetrahydropyridine.

5. Thiazole derivatives according to claim 1, wherein $R^2$ is hydrogen, $C_1$–$C_6$ alkyl, $C_1$–$C_6$ alkoxy, phenyl or amino, and wherein if $R^2$ is amino it may be substituted by $C_1$–$C_6$ alkyl, $C_1$–$C_{13}$ acyl, $C_2$–$C_7$ alkyloxycarbonyl, $C_3$–$C_7$ alkenyloxycarbonyl, $C_7$–$C_{14}$ aralkyloxycarbonyl, or wherein $R^2$ may be part of a piperazine, or a N—($C_1$–$C_6$ alkyl) substituted piperazine ring.

6. Thiazole derivatives according to claim 5, wherein $R^1$ is a halogen or CN, $R^2$ is an unsubstituted or substituted amino group, and $R^3$ is $C_1$–$C_4$ alkyl or arylethyl.

7. Thiazole derivatives according to claim 6, wherein $R^1$ is Cl and the thiazole is connected to position 3 of the tetrahydropyridine.

8. Thiazole derivatives according to claim 6, wherein $R^1$ is CN and the thiazole is connected to position 3 of the tetrahydropyridine.

9. Thiazole derivatives comprising the general formula:

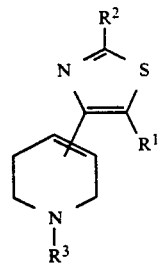

[I]

wherein
$R^1$ is a halogen, $CF_3$, CN, $NO_3$, OH or $C_1$–$C_6$ alkoxy;
$R^2$ is H, $C_1$–$C_6$ alkyl, $C_1$–$C_6$ alkoxy, aryl, selected from the group consisting of phenyl, naphthyl, pyridyl or thienyl wherein the phenyl, naphthyl, pryridyl, and thienyl may be substituted by OH, halogen, $CF_3$, CN, $NO_2$, $C_1$–$C_6$ alkyl and $C_1$–$C_6$ alkoxy, $C_6$–$C_{13}$ aralkyl, and an unsubstituted amino group, an amino group substituted by a compound selected from the group consisting of $C_1$–$C_6$ alkyl, $C_1$–$C_{13}$ acyl, said aryl as defined above, $C_6$–$C_{13}$ aralkyl, $C_1$–$C_6$ alkyloxycarbonyl, $C_2$–$C_6$ alkenyloxycarbonyl and $C_6$–$C_{13}$ aralkyloxycarbonyl or a substituted amino group the nitrogen atom of which is part of a 5 or 6 membered ring selected from the group consisting of pyrrolidine, imidazolidine, pyrimidine, morpholine, piperidine, unsubstituted or N—($C_1$–$C_6$ alkyl) substituted piperazine;
$R^3$ is $C_1$–$C_6$ hydrocarbon, $C_6$–$C_{13}$ aralkyl, $C_2$–$C_7$ alkoxy-alkyl or $C_1$–$C_{13}$ acyl;
and their pharmaceutically acceptable acid addition salts.

10. Thiazole derivatives according to claim 9, wherein $R^1$ is a halogen or CN, $R^2$ is an unsubstituted or substituted amino group, and $R^3$ is $C_1$–$C_4$ alkyl or arylethyl.

11. Thiazole derivatives according to claim 10, wherein $R^1$ is Cl and the thiazole is connected to position 3 of the tetrahydropyridine.

12. Thiazole derivatives according to claim 10, wherein $R^1$ is CN and the thiazole is connected to position 3 of the tetrahydropyridine.

13. A pharmaceutical composition comprising a thiazole derivative according to claim 9 in an effective amount for treating depression, anxiety disorders or cognitive disturbances and a pharmaceutically acceptable carrier.

14. A method for the treatment of depression, anxiety disorders for cognitive disturbances in a patient, comprising administering an effective amount of a pharmaceutical composition according to claim 13 to said patient.

* * * * *